(12) United States Patent
Miyajima

(10) Patent No.: US 10,495,617 B2
(45) Date of Patent: Dec. 3, 2019

(54) $CO_2$ SENSOR REFERENCE VALUE CALIBRATION APPARATUS AND METHOD FOR CALIBRATING REFERENCE VALUE OF $CO_2$ SENSOR

(71) Applicant: DENSO WAVE INCORPORATED, Chita-gun, Aichi-pref. (JP)

(72) Inventor: Takahiro Miyajima, Chita-gun (JP)

(73) Assignee: DENSO WAVE INCORPORATED, Aichi-Pref. (JP)

(*) Notice: Subject to any disclaimer, the term of this patent is extended or adjusted under 35 U.S.C. 154(b) by 275 days.

(21) Appl. No.: 15/355,166

(22) Filed: Nov. 18, 2016

(65) Prior Publication Data

US 2017/0248564 A1    Aug. 31, 2017

(30) Foreign Application Priority Data

Feb. 29, 2016 (JP) .................................. 2016-037156

(51) Int. Cl.
*G01N 33/00* (2006.01)

(52) U.S. Cl.
CPC ....... *G01N 33/0006* (2013.01); *G01N 33/004* (2013.01); *G01N 33/0073* (2013.01)

(58) Field of Classification Search
CPC ............. G01N 33/0006; G01N 33/004; G01N 33/0073; Y02A 50/244
USPC .......................................................... 73/1.03
See application file for complete search history.

(56) References Cited

U.S. PATENT DOCUMENTS

2006/0173637 A1* 8/2006 Martin ................... G01D 3/036
702/24

FOREIGN PATENT DOCUMENTS

| JP | H03-162659 A | 7/1991 |
| JP | H11-014590 A | 1/1999 |
| JP | 2014-115175 A | 6/2014 |
| JP | 2014173799 A * | 9/2014 |

OTHER PUBLICATIONS

Schell, Demand Control Ventilation Using CO2, Feb. 2001, ASHRAE Journal (Year: 2001).*

* cited by examiner

*Primary Examiner* — Eric S. McCall
*Assistant Examiner* — Timothy P Graves
(74) *Attorney, Agent, or Firm* — Oliff PLC

(57) ABSTRACT

A controller as a $CO_2$ sensor reference value calibration apparatus calibrates a reference value of the $CO_2$ sensor in the following manner. Introduction of outside air is started after a person is not detected. A $CO_2$ concentration, which is acquired when a preset first waiting time elapses, is set as a provisional reference value. The carbon dioxide concentration, which is acquired when a preset second waiting time elapses, is compared with the provisional reference value. In a case where a change rate of the carbon dioxide concentration is out of a preset allowable range, the carbon dioxide concentration is acquired when the second waiting time elapses after newly setting the acquired carbon dioxide concentration as the provisional reference value. In a case where the change rate of the carbon dioxide concentration is in the allowable range, the currently set provisional reference value is set as the reference value.

8 Claims, 5 Drawing Sheets

$CO_2$ SENSOR REFERENCE VALUE CALIBRATION APPARATUS AND METHOD FOR CALIBRATING REFERENCE VALUE OF $CO_2$ SENSOR

CROSS REFERENCE TO RELATED APPLICATION

This application is based on Japanese Patent Application No. 2016-037156 filed on Feb. 29, 2016, the disclosure of which is incorporated herein by reference.

TECHNICAL FIELD

The present disclosure relates to a $CO_2$ sensor reference value calibration apparatus for calibrating a reference value of a $CO_2$ sensor used for an air conditioning system. The present disclosure further relates to a method for calibrating the reference value of the $CO_2$ sensor.

BACKGROUND

An air conditioning system for performing air conditioning inside an object space has been known. Such an air conditioning system is provided with a $CO_2$ sensor for acquiring a carbon dioxide concentration (hereinafter, referred to as $CO_2$ concentration) in the object space and for introducing outside air such that the $CO_2$ concentration is controlled not to be excessively increased in the object space.

In a case of such a $CO_2$ sensor, a reference value may be deviated due to aging. In consideration of this, the reference value is required to be calibrated or corrected after installing the $CO_2$ sensor. Note that, in a case of the air conditioning system which is installed in general homes or general offices in a building, it is difficult to prepare a test environment. Therefore, in some cases, the calibration is performed based on, as reference, a $CO_2$ concentration in the atmosphere. For example, Patent Literature 1 discloses automatic calibration of the reference value of the $CO_2$ sensor based on the $CO_2$ concentration in the atmosphere. In the configuration of Patent Literature 1, the $CO_2$ concentration of the outside air is assumed to be approximately 400 ppm.

(Patent Literature 1)
Publication of Japanese unexamined patent application No. 2014-115175

However, in the configuration of Patent Literature 1, the calibrated reference value is not necessarily matched with the $CO_2$ concentration in the atmosphere (outside air). Specifically, in Patent Literature 1, an environment, in which a person is resident for 24 hours, is assumed. In the environment where a person exists in the object space, carbon dioxide ($CO_2$) is necessarily emitted. In this case, if an introduction amount of the outside air and an emission amount of $CO_2$ are balanced with each other, it is considered that the $CO_2$ concentration becomes constant. Nevertheless, in the present condition, $CO_2$ is being emitted. For this reason, the reference value, which is calibrated in such a condition, may have an offset, by which the reference value is increased with respect to the $CO_2$ concentration in the atmosphere.

SUMMARY

It is an object of the present disclosure to produce a $CO_2$ sensor reference value calibration apparatus configured to accurately match a reference value of a $CO_2$ sensor with a $CO_2$ concentration in the atmosphere. It is another object of the present disclosure to produce a method for calibrating the reference value of the $CO_2$ sensor.

According to an aspect of the present disclosure, a $CO_2$ sensor reference value calibration apparatus includes a person detection unit, a $CO_2$ sensor, a clock unit that measures time, and a calibration unit that calibrates a reference value of the $CO_2$ sensor. As described above, in the environment where a person is present in the object space, $CO_2$ is necessarily emitted. Consequently, the reference value, which is calibrated in such a situation, is set to have an offset by which the reference value is increased with respect to the $CO_2$ concentration in the atmosphere. In consideration of this, it is assumable to calibrate the reference value of the $CO_2$ sensor after a person is not detected in the object space any longer, thereby to avoid the increased offset.

More specifically, a configuration is employed to start introduction of the outside air after a person is not detected in the object space any longer. In addition, a $CO_2$ concentration, which is acquired when a preset first waiting time has elapsed after starting the introduction of the outside air, is set as a provisional reference value. In the present configuration, the acquiring of the $CO_2$ concentration is started in a state where the object space is ventilated to some extent. In other words, the $CO_2$ concentration is not acquired in a period in which the $CO_2$ concentration is assumed to be obviously decreasing. In this way, unnecessary power consumption can be reduced.

In addition, a configuration is employed to compare a $CO_2$ concentration, which is acquired when a preset second waiting time has elapsed after setting a provisional reference value, with the provisional reference value. In a case where a change rate of the $CO_2$ concentration is out of an allowable range, the acquired $CO_2$ concentration is set as a new provisional reference value. In this case, subsequently, the $CO_2$ concentration is acquired again when the second waiting time has elapsed. The present configuration enables to avoid erroneous calibrations in a state where the $CO_2$ concentration is decreasing. In the present configuration, the allowable range may be determined based on, for example, an accuracy of the $CO_2$ sensor.

On the other hand, in a case where the change rate of the $CO_2$ concentration is in the allowable range, the reference value of the $CO_2$ sensor is calibrated by setting the currently set provisional reference value as the reference value. The present configuration enables to calibrate the reference value of the $CO_2$ sensor in a state where the change in the $CO_2$ concentration is in the allowable range, that is, in a state where the object space is almost the same as the outside air. Accordingly, the present configuration enables to accurately match the reference value of the $CO_2$ sensor with the $CO_2$ concentration in the atmosphere.

According to an aspect of the present disclosure, the calibration unit compares the $CO_2$ concentration, which is acquired when the second waiting time has elapsed, with the provisional reference value. In a case where the acquired $CO_2$ concentration is smaller than the provisional reference value and where the change rate of the $CO_2$ concentration is negative, the calibration unit sets the acquired $CO_2$ concentration as a new provisional reference value. Subsequently, the calibration unit acquires the $CO_2$ concentration again when the second waiting time has elapsed. That is, it is considered that in a state where the $CO_2$ concentration is still being decreasing, the $CO_2$ concentration is greater than that of the outside air. Therefore, it is required to wait until the $CO_2$ concentration has decreased sufficiently.

On the other hand, in a case where the acquired $CO_2$ concentration is equal to or greater than the provisional reference value and where the change rate of the $CO_2$ concentration is positive, the currently set provisional reference value is set as the reference value. The present configuration enables to calibrate the reference value of the $CO_2$ sensor in a state where the decrease in the $CO_2$ concentration has ceased, that is, in a state where the object space is the same as the outside air.

According to an aspect of the present disclosure, at the time of setting the provisional reference value, the calibration unit sets a value, which is acquired by correcting the acquired $CO_2$ concentration based on a preset error correction value, as the provisional reference value. General homes and offices are assumed as the object spaces. Therefore, air in the object space likely fluctuates to cause a change in the distribution of the $CO_2$ concentration detected by the $CO_2$ sensor. In addition, it is likely that a detection value of the $CO_2$ sensor has an error. That is, in a case where the inside of the object space is in a significantly natural state, the $CO_2$ concentration is not necessarily stable and is not necessarily at a constant value, even after the $CO_2$ concentration has continually decreased such that the $CO_2$ concentration is almost the same as that of the outside air. In this case, because of being in the natural state, the $CO_2$ concentration may be rather easily changeable. In this regard, the present configuration sets a value, which is acquired by correcting the acquired $CO_2$ concentration based on the error correction value, as the provisional reference value. In this way, the reference value can be calibrated to absorb the air fluctuation and the error of the $CO_2$ sensor.

According to an aspect of the present disclosure, the first waiting time is set based on a maximum allowable value of the $CO_2$ concentration with respect to a living space and based on a preset amount of ventilation air with respect to the living space. That is, the first waiting time is set as the assumed maximum ventilation time. In the present configuration, the calibrating of the reference value can be started when it is assumed that the object space is almost the same as the outside air, that is, when it is assumed that the air in the object space is almost replaced with the outside air.

According to an aspect of the present disclosure, the first waiting time is set based on the $CO_2$ concentration at the time of starting the introduction of the outside air and the preset amount of ventilation air with respect to the living space. For example, it is generally assumed that the $CO_2$ concentration in the object space is not so high in a case where a person is not present at the time for the calibration. In such a case, it is considered that the time until the state where the object space becomes the same as the state of the outside air becomes shorter. In consideration of this, the first waiting time is set based on the $CO_2$ concentration at the time of starting the introduction of the outside air. In this way, the time for calibration can be reduced.

In addition, it is likely that the reference value of the $CO_2$ sensor is gradually deviated due to the aging. Therefore, in some cases, the $CO_2$ sensor may detect a value which is higher than an actual value of the $CO_2$ concentration. In such a case, ventilation is performed based on the $CO_2$ concentration which is higher than the actual $CO_2$ concentration. Even in such a case, it can be assumed that the ventilation is sufficiently performed by a necessary amount when the first waiting time has elapsed. In this case, the time for the calibration of the reference value can be reduced. Note that, in a case where the reference value of the $CO_2$ sensor is deviated, the $CO_2$ sensor may detect, for example, the $CO_2$ concentration which is lower than the actual $CO_2$ concentration. Even in this case, the reference value is finally determined based on the change rate of the $CO_2$ concentration. Therefore, it is less likely that the reference value is incorrectly set.

According to another aspect of the present disclosure, a $CO_2$ sensor reference value calibration method includes detecting a person in an object space. The method further includes starting introduction of outside air after a person is not detected in an object space. The method further includes setting a provisional reference value by acquiring a carbon dioxide concentration when a preset first waiting time elapses after starting the introduction of the outside air. The method further includes calibrating a reference value of a $CO_2$ sensor. The calibrating includes comparing the carbon dioxide concentration, which is acquired when a preset second waiting time elapses after setting the provisional reference value, with the provisional reference value. The calibrating further includes setting the acquired carbon dioxide concentration as a new provisional reference value, and then acquiring the carbon dioxide concentration when the second waiting time elapses, in a case where the acquired carbon dioxide concentration is lower than the provisional reference value. The calibrating further includes setting the currently set provisional reference value as the reference value in a case where the acquired carbon dioxide concentration is equal to or greater than the provisional reference value.

As described above, when the reference value of the $CO_2$ sensor is calibrated by using such a method, the reference value of the $CO_2$ sensor can be accurately matched with the $CO_2$ concentration in the atmosphere.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

Figure 1:
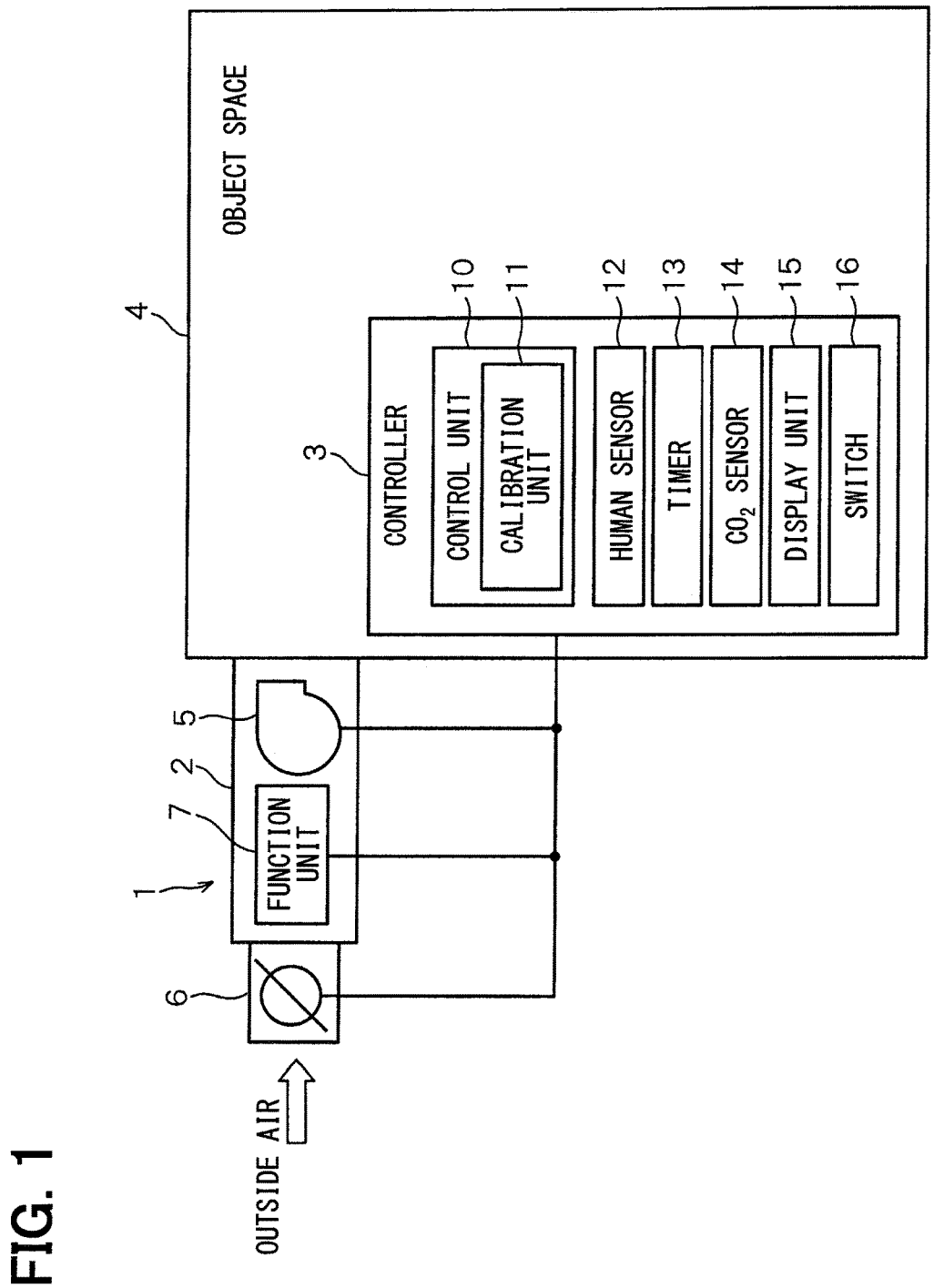
FIG. 1 is a diagram schematically illustrating a configuration of an air conditioning system according to an embodiment.

Hereinafter, embodiments of the present disclosure will be described with reference to FIG. 1 to FIG. 3. As shown in FIG. 1, an air conditioning system 1 of the present embodiment is provided with an air conditioning unit 2 and a controller 3. A well-known configuration may be employed as the air conditioning unit 2. Therefore, the detailed description of the air conditioning unit 2 is omitted. The air conditioning unit 2 includes a blower fan 5, an introduction-side damper 6, a function unit 7, and/or the like. The blower fan 5 is for introducing air. The introduction-side damper 6 is configured to adjust an introduction amount of the introduced air by controlling its opening degree. The function unit 7 adjusts temperature and humidity of the introduced air.

The controller 3 functions as an operation input unit for inputting an operation with respect to the air conditioning system 1 by a user. The controller 3 may be generally provided on a wall in the object space 4. The controller 3 includes a control unit 10, a calibration unit 11, a human sensor 12, a timer 13, a $CO_2$ sensor 14, a display unit 15, and a switch 16. The controller 3 functions as a reference value calibration apparatus.

The control unit 10 is configured with a microcomputer including, for example, a CPU, a ROM, and a RAM which are not shown in the drawings. The control unit 10 controls the controller 3 by executing a program which is stored in the ROM and/or the like. Specifically, the control unit 10 displays a temperature of the object space 4 on the display unit 15. In addition, the control unit 10 controls the air conditioning unit 2 based on an instruction input from the switch 16. Furthermore, the control unit 10 adjusts the amount of air introduced into the object space 4 by controlling the opening degree of the introduction-side damper 6. Hereinafter, for the sake of convenience, the amount of air introduced into the object space 4 is referred to as an introduction amount of the air.

The control unit 10 is provided with the calibration unit 11. In the present embodiment, the calibration unit 11 enables the calibration with the program executed by the control unit 10. That is, the calibration unit 11 is in a form of software. The calibration unit 11 calibrates the reference value of the $CO_2$ sensor 14 based on the $CO_2$ concentration (carbon dioxide concentration) in the object space 4. Details of the calibration will be described below. Note that, the calibration corresponds to correction.

The human sensor 12, which detects a person in the object space 4, functions as a person detection unit. The human sensor 12 detects a person in the object space 4 by infrared, ultrasonic wave, visible light, or a combination thereof. That is, the human sensor 12 detects the presence of the person in the object space 4.

The timer 13, which measures a time, functions as a clock unit. In the present embodiment, as the timer 13, a so-called real time clock is employed. The timer 13 has so-called a calendar function of specifying the date and the time. In addition, the timer 13 is also configured to measure the time that has elapsed from a certain point of time. The timer 13 may be built in the control unit 10.

The $CO_2$ sensor 14 acquires the $CO_2$ concentration in the object space 4. The $CO_2$ sensor 14 acquires the $CO_2$ concentration as a relative value with respect to a preset reference value. The display unit 15 includes, for example, a liquid crystal panel and/or the like. The display unit 15 displays the temperature in the object space 4, a current operation state, and/or the like. The switch 16 includes, for example, a mechanical switch and/or a touch panel which is provided corresponding to the display unit 15. A user manipulates the switch 16 to provide an instruction of a set temperature, an instruction for turning-on to start the operation, and an instruction for turning-off to stop the operation.

Next, operation of the above-described configuration will be described. As described above, the $CO_2$ sensor 14 acquires the $CO_2$ concentration as a relative value with respect to the preset reference value. For this reason, in a case where the reference value is deviated, the acquired $CO_2$ concentration is also deviated from the actual concentration. Thus, it is required to correctly reset the reference value, that is, it is required to calibrate the $CO_2$ sensor. In consideration of the deviation of the reference value due to the aging, the reference value is desirably calibrated at a frequency of about, for example, once several months or once a year. In addition, it is considered that the calibration of the reference value of the $CO_2$ sensor 14 is preferably performed in a test environment at the $CO_2$ concentration which is deemed to be a reference value.

However, in a case where the air conditioning system 1 is installed in, for example, general homes or offices in a building, it is difficult to prepare the above-described test environment. In this regard, in the present embodiment, the reference value of the $CO_2$ sensor 14 is calibrated in a way described below. Note that, the following processes may be performed by the calibration unit 11 or the like; however, in the embodiment, the controller 3 is described as a main component for the sake of simplicity of explanation.

Figure 2:
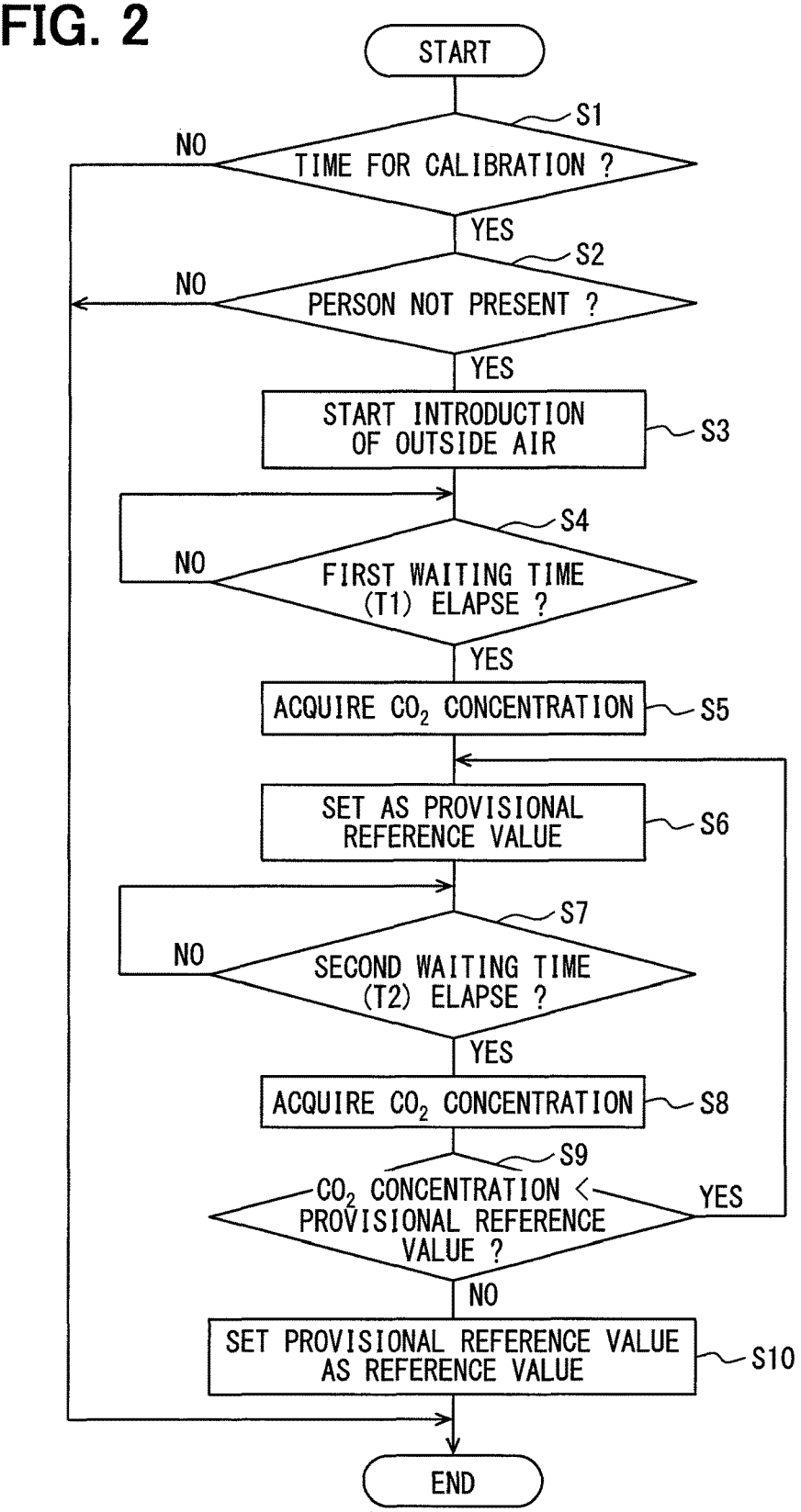
FIG. 2 is a flowchart showing a reference value calibration process implemented by a calibrating apparatus.

The controller 3 performs the reference value calibration process illustrated in FIG. 2. The reference value calibration process shows the flow of a reference value calibration method. The controller 3 determines whether or not it is a time for the calibration of the reference value (S1). Herein, the time for the calibration represents a preset date and time or represents a certain point of time at which a predetermined time period has elapsed from the previous calibration. In the present embodiment, it is assumed that the calibration is performed once a year. In addition, the time for the calibration may be set to be midnight, at which time a person is not present in the object space, so as to easily perform the process after step S2 described below. When it is determined that it is not the time for the calibration (S1: NO), the controller 3 completes the process.

On the other hand, when it is determined that it is the time for the calibration (S1: YES), the controller 3 determines whether or not a person is present in the object space (S2). In a case where a person is not present in the object space (S2: NO), the controller 3 completes the process. The reason is as follows. In a case where a person is present in the object space, $CO_2$ (carbon dioxide) is emitted as the person's breathing, and thus it is concerned that the reference value cannot be appropriately calibrated.

In contrast, when it is determined that a person is not present in the object space (S2: YES), the controller 3 determines that a condition for appropriate calibration of the reference value is made. Thus, the controller 3 starts the introduction of the outside air into the object space 4 (S3). At this time, the controller 3 introduces the outside air into the object space 4 by driving the blower fan 5 and adjusting the opening degree of the introduction-side damper 6. In other words, the controller 3 ventilates the inside of the object space 4 such that the state in the object space 4 becomes the same as that of the outside air.

Figure 3:
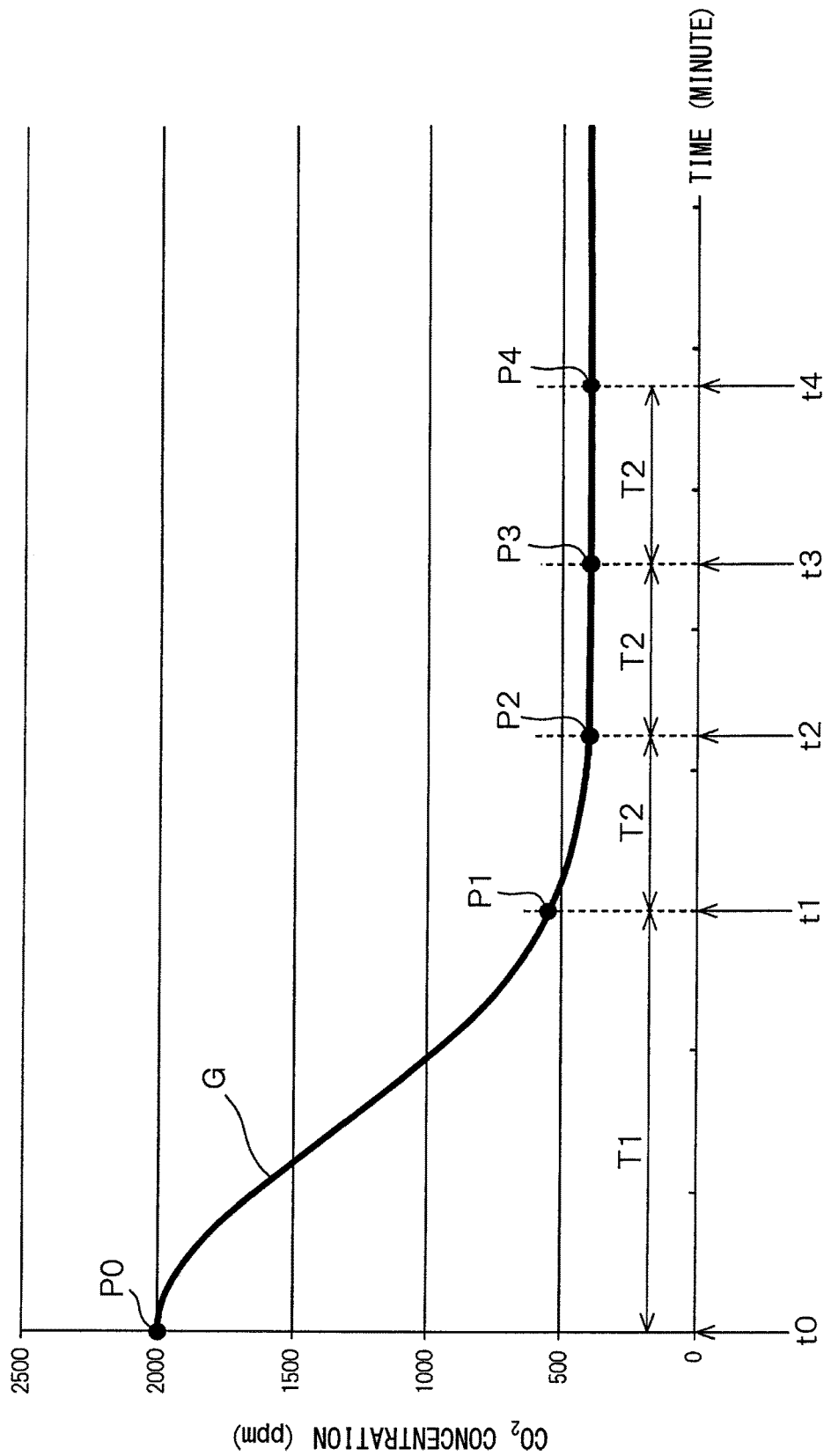
FIG. 3 is a graph showing an example of change in a $CO_2$ concentration over time.

FIG. 3 illustrates a graph G as an example of change in the $CO_2$ concentration over time in the object space 4 after starting the introduction of the outside air. FIG. 3 illustrates a state where the introduction of the outside air at the time (t0) is started and where the $CO_2$ concentration at the time (t0) is at the point P0. In this case, it is expected that the $CO_2$ concentration in the object space 4 is basically decreased as the time elapses after the outside air is introduced. In addition, it is considered that the $CO_2$ concentration in the object space 4 is continually at a constant value so as to be almost the same as the $CO_2$ concentration of the outside air at the time point at which the ventilation of the inside of the object space 4 is completed, that is, at the time point at which the inside of the object space 4 is sufficiently ventilated and thus the state in the object space 4 is the same as that of the outside air.

For this reason, it is considered to calibrate the reference value in a state where the $CO_2$ concentration in the object space 4 is the same as the $CO_2$ concentration of the outside air, thereby to appropriately match the reference value with the $CO_2$ concentration of the outside air. That is, in that state, the reference value can be appropriately calibrated. Meanwhile, in a case of general homes or offices in a building, it is expected that many people come in and go out frequently. In this case, the amount of $CO_2$ emission is changed depending on the number of people. From this aspect, in the configuration to simply wait until determination is made that the inside of the object space 4 is sufficiently ventilated, it is necessary to set a sufficiently long ventilation time, during which ventilation is continued, in order to cope with the change in the number of people.

It is considered, in the configuration to simply wait until a predetermined time has elapsed, that as the ventilation time becomes longer, it is highly likely that people come in and go out. Consequently, it is highly likely that the calibration of the reference value is not appropriately performed due to the people coming in and out. For this reason, the reference value of the $CO_2$ sensor 14 is desirably calibrated in a short time.

In addition, it is conceivable to set a long ventilation time in order to ventilate the inside of the object space until determination is made that the ventilation is sufficiently performed. In this case, it may be also considered that the inside of the object space has been already ventilated before elapsing the long ventilation time. Consequently, in this case, unnecessary power consumption is likely to be caused. In addition, in a configuration where the $CO_2$ concentration is repeatedly acquired after starting the introduction of the outside air and where the ventilation state is determined based on the change in the $CO_2$ concentration, the $CO_2$ concentration may be acquired even in a state where the ventilation is not sufficiently performed. In this case, unnecessary power consumption is likely to be caused.

In consideration of this, the controller 3 waits until determination is made that the ventilation is performed to some extent after starting the introduction of the outside air. Subsequently, on the basis of the change in the $CO_2$ concentration, the controller 3 determines whether or not the state of air in the object space 4 is the same as that of the outside air. The time, which is for waiting until determination is made that the ventilation is performed to some extent, corresponds to a first waiting time. In the present embodiment, the first waiting time is set as follows.

In a case of the United States, the amount of ventilation air is determined to be 0.54 $m^3/h*m^2$ based on ASHRAE standard 62.2. For this reason, ventilation is performed by 0.54 $m^3/h$ per unit area with respect to a general living space. Further, the maximum allowable value of the $CO_2$ concentration with respect to a living space such as general homes is defined as 2000 ppm. That is, in a case where the living space is set to be an object, the maximum value of the $CO_2$ concentration is presumed to be 2000 ppm. Note that, the ventilation of the inside the object space 4 having a large amount of ventilation air can be performed in a short time under the condition that the object spaces 4 have the same size.

On that bases, it can be determined that the ventilation of the inside of the object space 4 is completed to some extent by performing the ventilation of 0.54 $m^3/h$ per unit area and by waiting until the $CO_2$ concentration changes from 2000 ppm to be the same as that of the outside air. That is, the first waiting time can be set based on the maximum allowable value of the carbon dioxide concentration with respect to a living space. The amount of ventilation air which is defined in advance with respect to the living space.

Further, the required time until it can be determined that the ventilation is completed is changed depending of the size of the object space 4. It is noted that, in a case where the object space 4 has a standard size, such as a living room of general homes, the time for the ventilation is estimated to be approximately 80 minutes, for example. That is, it is estimated that when the ventilation is performed for 80 minutes in a state where a person is not present, the air in the object space 4 is replaced with the outside air.

As such, in the present embodiment, the first waiting time is set based on the maximum allowable value of the $CO_2$ concentration (here, 2000 ppm) with respect to a living space and the amount of ventilation air (here, 0.54 $m^3/h*m^2$) which is defined in advance with respect to the living space. In consideration that living spaces are in different sizes in reality, the first waiting time of the present embodiment is set to be 120 minutes with a sufficient margin.

Meanwhile, when the introduction of the outside air is started in step S3 of the reference value calibration process as shown in FIG. 2, the controller 3 determines whether or not the above-described first waiting time (T1, refer to FIG. 3) has elapsed (S4). When it is determined that the first waiting time (T1) has not elapsed yet (S4: NO), the process proceeds to step S4, and the controller 3 waits until the first waiting time has elapsed. In addition, in a case where a person is detected during the first waiting time (T1), the controller 3 stops the reference value calibration process. Further, the first waiting time (T1) and a second waiting time (T2, refer to FIG. 3) described below are counted by the timer 13.

On the other hand, when it is determined that the first waiting time (T1) has elapsed (S4: YES), the controller 3 acquires the $CO_2$ concentration (S5). In step S5, the controller 3 acquires the $CO_2$ concentration based on the preset reference value. At this time, the acquired $CO_2$ concentration corresponds to a value at the point P1 at the time (t1) illustrated in FIG. 3. In addition, the controller 3 sets the $CO_2$ concentration acquired in step S5 as a provisional reference value (S6). Note that, in the present embodiment, the acquired $CO_2$ concentration is set as the provisional reference value as it is.

Subsequently, the controller 3 determines whether or not the second waiting time (T2) has elapsed (S7). In the present embodiment, the second waiting time is the preset value and is set to be 8 minutes which is 1/10 of the first waiting time. Note that, the second waiting time is not limited to the 8 minutes and may be properly set to be in a range of several minutes to several tens of minutes.

When it is determined that the second waiting time has not elapsed yet (S7: NO), the process proceeds to step S7 at which the controller 3 waits until the second waiting time has elapsed. In a case where a person is detected during the second waiting time (T2), the controller 3 stops the reference value calibration process.

On the other hand, when it is determined that the second waiting time has elapsed (S7: YES), the controller 3 determines the $CO_2$ concentration based on the provisional reference value, which is set in step S6, as a reference (S8). In addition, the controller 3 determines whether or not the $CO_2$ concentration acquired in step S8 is smaller than the provisional reference value set in step S6 (S9). That is, the controller 3 determines whether or not the change rate of the $CO_2$ concentration is negative. In addition, in the present embodiment, the change rate of the $CO_2$ concentration is calculated by establishing the following expression.

$$\text{Change rate of } CO_2 \text{ concentration} = \text{acquired } CO_2 \text{ concentration} - \text{provisional reference value} \quad (1)$$

In this case, in a case where the acquired $CO_2$ concentration is smaller than the provisional reference value, that is, in a case where the change rate of $CO_2$ concentration is negative, it is considered that the $CO_2$ concentration is still decreased. For this reason, when it is determined that the $CO_2$ concentration is smaller than the provisional reference value (S9: YES), the process proceeds to step S6. The controller 3 sets the acquired $CO_2$ concentration as a new provisional reference value (S6). Subsequently, the controller 3 waits until the second waiting time has elapsed (S7). Such a situation corresponds to time (t2) and time (t3) as shown in FIG. 3. In other words, the $CO_2$ concentration at the point P2 is smaller than the $CO_2$ concentration at the point P1 which is set as an initial provisional reference value. In addition, the $CO_2$ concentration at the point P3 is smaller than the $CO_2$ concentration at the point P2 which is set as a new provisional reference value.

In contrast, when it is determined that the $CO_2$ concentration is not smaller than the provisional reference value, that is, when it is determined that the $CO_2$ concentration acquired in step S8 is equal to or greater than the currently set provisional reference value (S9: NO), the controller 3 sets the currently set provisional reference value as a reference value (S10). The present situation corresponds to the point P4 as shown in FIG. 3. The $CO_2$ concentration at the point P4 is equal to or greater than the $CO_2$ concentration at the point P3 which is set as the provisional reference value. That is, when it is determined that the change rate of $CO_2$ concentration is positive, the controller 3 sets the currently set provisional reference value as the reference value.

In step S10, the $CO_2$ concentration at the minimum value is set as the reference value among the acquired $CO_2$ concentrations, which are acquired until the $CO_2$ concentration becomes continually at an almost constant value after starting the introduction of the outside air. In the present configuration, the $CO_2$ concentration, in a state where the $CO_2$ concentration in the object space 4 is continually at an almost constant value, is set as the new reference value. That is, the $CO_2$ concentration, which is almost matched with that of the outside air, is set as the new reference value. In this way, the controller 3 calibrates the reference value of the $CO_2$ sensor 14 by setting the $CO_2$ concentration, when it is determined that the air in the object space 4 is almost matched with the outside air, as the new reference value.

According to the above-described embodiment, the following effects can be acquired. The controller 3 starts the introduction of the outside air after a person is not detected in the object space 4 any longer. The controller 3 sets the $CO_2$ concentration, which is acquired when the preset first waiting time has elapsed after starting the introduction of the outside air, as the provisional reference value. In the present configuration, acquiring of the $CO_2$ concentration is started in a state where the ventilation is performed to some extent. In other words, the $CO_2$ concentration is not acquired during a period in which the $CO_2$ concentration is assumed to be obviously decreased. Thus, in the present configuration, unnecessary power consumption can be reduced.

In addition, the controller 3 acquires the $CO_2$ concentration when the preset second waiting time has elapsed after setting the provisional reference value. The controller 3 compares the acquired $CO_2$ concentration with the provisional reference value. In a case where the acquired $CO_2$ concentration is smaller than the provisional reference value, that is, in a case where the change rate of the $CO_2$ concentration is negative, the controller 3 sets the acquired $CO_2$ concentration as a new provisional reference value. The controller 3 further acquires the $CO_2$ concentration again when the second waiting time has elapsed.

On the other hand, in a case where the acquired $CO_2$ concentration is equal to or greater than the provisional reference value, that is, in a case where it is determined that the change rate of $CO_2$ concentration is positive, the controller 3 sets the currently set provisional reference value as the reference value. In the present configuration, erroneous calibrations can be avoided while the $CO_2$ concentration is decreased. Thus, the reference value of the $CO_2$ sensor 14 can be calibrated in the state where the decrease in the $CO_2$ concentration has ceased, that is, in a state where the state in the object space 4 is the same as that of the outside air.

Accordingly, the reference value of the $CO_2$ sensor 14 can be accurately matched with the $CO_2$ concentration in the atmosphere.

The controller 3 sets the first waiting time based on the maximum value of the $CO_2$ concentration, which is allowable for a living space, and the preset amount of ventilation air with respect to the living space. In the present configuration, even in a case where the object space 4 has a different size, the first waiting time at the same value can be used. Thus, the versatility can be improved.

In addition, when the reference value of the $CO_2$ sensor 14 is calibrated by using the reference value calibration method as shown in FIG. 2, as described above, the reference value of the $CO_2$ sensor 14 can be accurately matched with the $CO_2$ concentration in the atmosphere.

Other Embodiments

The present disclosure is not limited to the configuration exemplified in the above-described embodiments, and can be optionally modified or expanded without departing from the scope.

Figure 4:
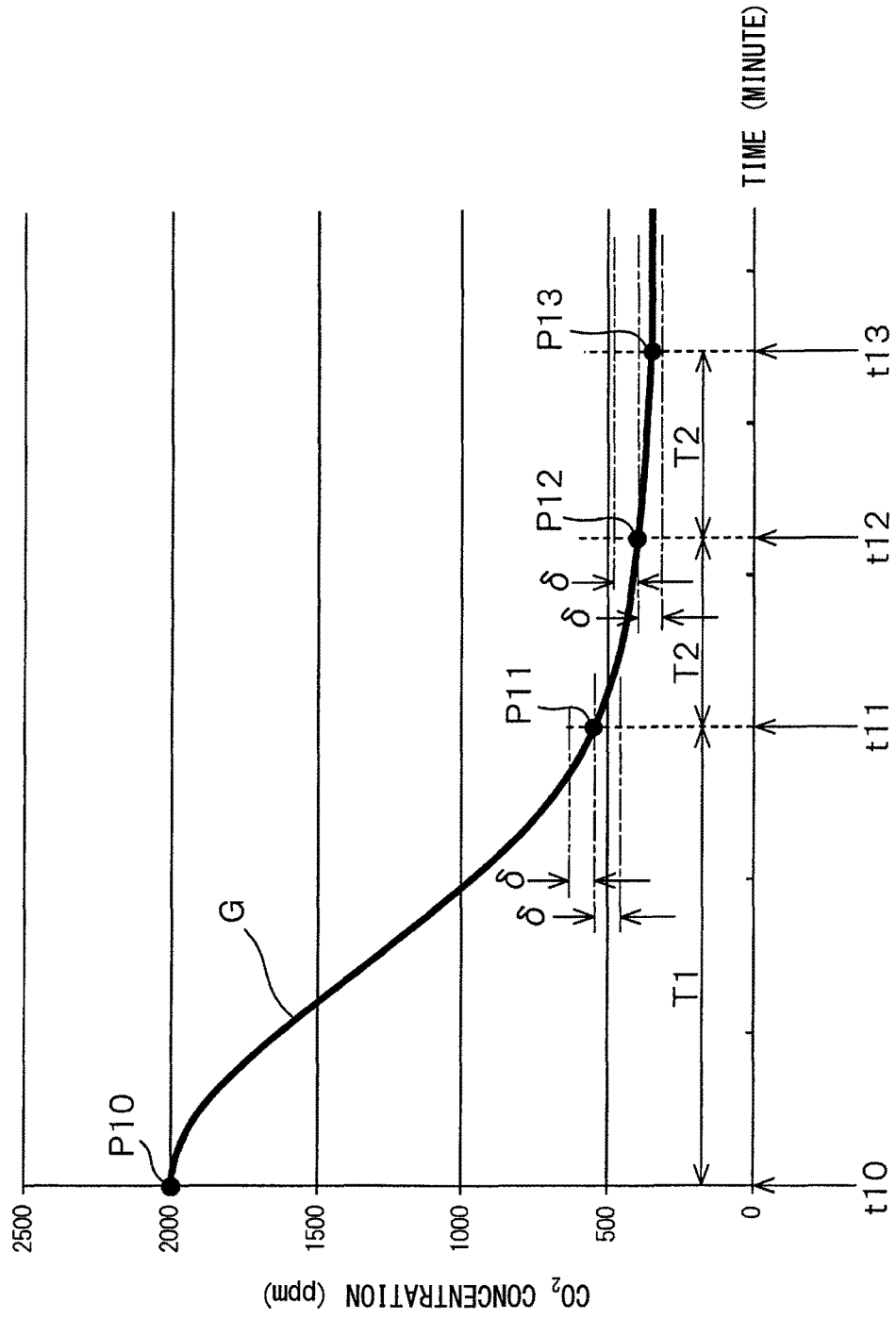
FIG. 4 is a graph showing an example of change in the $CO_2$ concentration over time according to another embodiment.

In the embodiment, an example, in which the reference value is calibrated in the case where it is determined that the change rate of the $CO_2$ concentration is positive, is described. It is noted that, even in a case where the change rate of the $CO_2$ concentration is negative, the reference value may be calibrated as long as the change rate is in a preset allowable range. For example, as shown in FIG. 4, it is assumed that the introduction of the outside air is started at the time (t10). Subsequently, the initial provisional reference value is set at the time (t11) when the first waiting time has elapsed. Subsequently, the $CO_2$ concentration is acquired at the time (t12) when the second waiting time has elapsed. In addition, on the basis of the $CO_2$ concentration at each point, the allowable range of the change amount of the $CO_2$ concentration is set in a range of $\pm\delta$. That is, the allowable range of the change rate of $CO_2$ concentration is set in a range of $\delta/T2$. Note that, the value $\delta$ may be set in consideration of an accuracy of the $CO_2$ sensor 14, the size of the object space 4, and/or the like.

As shown in FIG. 4, the $CO_2$ concentration at the point P12 is below the allowable range at the point P11. That is, the $CO_2$ concentration at the point P12 is out of the allowable range which is set with respect to the provisional reference value at the point P11, that is, at the current point. For this reason, the controller 3 sets a range of $\pm\delta$ as a new allowable range based on the $CO_2$ concentration at the point P12. In addition, the controller 3 waits until the second waiting time has elapsed and acquires the $CO_2$ concentration which is indicated at the point P13 at the time (t13).

At this time, the $CO_2$ concentration at the point P13 is within the allowable range at the point P12. For this reason, the change rate between the values of the $CO_2$ concentration at the two continuous measurement points is in the allowable range. Therefore, the controller 3 sets the $CO_2$ concentration at the point P13 as the reference value. In the present configuration, the reference value can be calibrated in a state where the change rate of the $CO_2$ concentration is small, that is, in a state where it can be determined that the $CO_2$ concentration is almost the same as that of the outside air.

In addition, the allowable range is set, and thus the reference value can be restricted from being erroneously calibrated. That is, the allowable range is set based on the accuracy of the $CO_2$ sensor 14, the size of the object space 4, and/or the like, as described above. In other words, the allowable range is considered in a range, in which air in the object space 4 is assumed to fluctuate in a natural state, and is considered in an error range of the $CO_2$ sensor 14.

Figure 5:
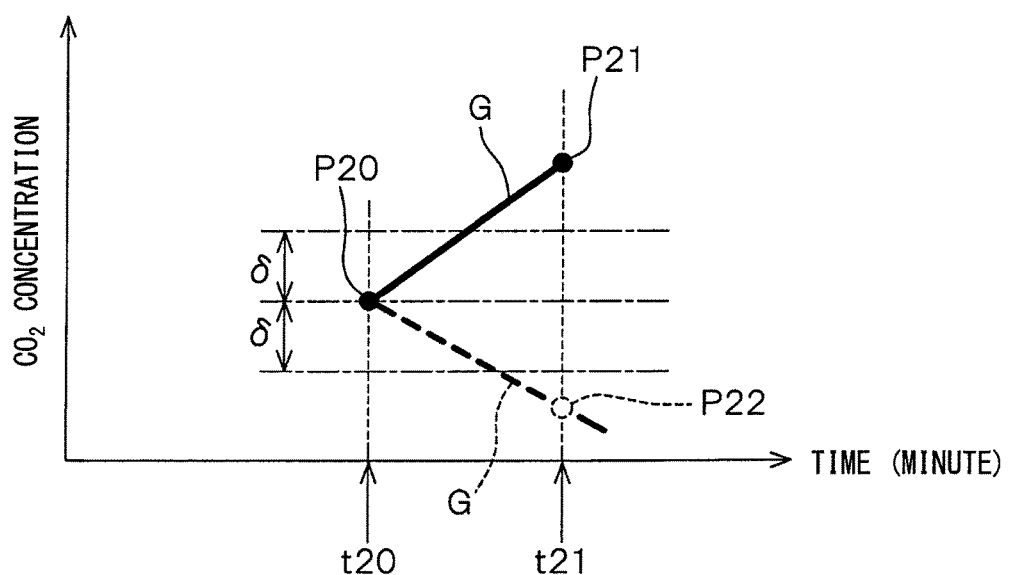
FIG. 5 is a graph showing an allowable range.

For example, as shown in FIG. 5, it is considered that a case where the $CO_2$ concentration is at the point P21 at the time (t21), which is beyond the allowable range with respect to the $CO_2$ concentration at the point P20 at the time (t20). FIG. 5 shows a state where the distribution of the $CO_2$ concentration in the object space 4 is deviated, that is, a state where the ventilation is not sufficiently performed. Therefore, even when the change rate of the $CO_2$ concentration is positive, in a case where the $CO_2$ concentration is beyond the allowable range, the reference value is not set based on the above-described change rate of the $CO_2$ concentration. In this case, the $CO_2$ concentration is obtained again after the second waiting time has elapsed such that the error caused by the air fluctuation and/or the like can be absorbed.

In addition, in a case where the $CO_2$ concentration is at the point P22, which is below the allowable range at the time (t21), it is considered that the $CO_2$ concentration in the object space 4 is still decreased or that the distribution of the $CO_2$ concentration in the object space 4 is deviated. In this case, the $CO_2$ concentration may be acquired again after the second waiting time has elapsed without setting the reference value based on the above-described $CO_2$ concentration. Note that, even in a case where the change rate of $CO_2$ concentration is negative, the reference value may be calibrated on condition that the absolute amount, which is the change amount in the $CO_2$ concentration, is in a range of $-\delta$, that is, on condition that the change rate of the $CO_2$ concentration is, for example, within a predetermined range.

In the embodiment, an example, in which the acquired $CO_2$ concentration is set as the provisional reference value, is described. It is noted that, a value acquired by calibrating the acquired $CO_2$ concentration based on a preset error correction value may be set as the provisional reference value. In consideration of the accuracy of the $CO_2$ sensor 14 as described above, a low value may be erroneously detected. In a case where the value is a minimum value, the minimum value, which is smaller than an appropriate value supposed to be the reference value, may be set as the reference value. In this regard, the error correction value may be preset in consideration of the accuracy of the $CO_2$ sensor 14, and/or the like. In this case, the $CO_2$ concentration, which is corrected by using the error correction value, may be set as the provisional reference value.

In the present configuration, the deviation of the distribution of the $CO_2$ concentration, which is caused by the air fluctuation, and an error of the accuracy of the $CO_2$ sensor 14 can be absorbed, and thereby the reference value can be restricted from being largely deviated. In this case, the error correction value may be statically determined or may be dynamically set based on a difference value between the previously acquired $CO_2$ concentration and the currently acquired $CO_2$ concentration and/or based on a moving average value of the acquired $CO_2$ concentrations.

In the embodiment, an example, in which the first waiting time is set based on the maximum value of the carbon dioxide concentration allowable for a living space and based on the preset amount of ventilation air with respect to the living space, is described. It is noted that, the first waiting time may be set based on the carbon dioxide concentration at the time of starting the introduction of the outside air and based on the preset amount of ventilation air with respect to the living space.

For example, in a case where a person is not present in the object space 4 at the time for the calibration, it is considered that the $CO_2$ concentration in the object space 4 is not the allowable maximum value. In this case, it is considered that the time required for the ventilation of the object space 4 is shorter as compared with a time required in a case of performing the ventilation in a state where the $CO_2$ concentration is maximum as described in the embodiment. In this case, the time for the calibration process can be shortened.

In the embodiment, an example in which the first waiting time is set based on ASHRAE standard 62.2. It is noted that, the first waiting time may be set based on other standards.

In addition, in the embodiment, the first waiting time is set in consideration of the area of the living space. It is noted that, it is considered that the first waiting time becomes longer in a specific space, which is larger than a general living space, such as a stairwell. For this reason, in a case where the first waiting time is calculated at, for example, 80 minutes, the first waiting time may be set with more sufficient margins such as at 160 minutes.

In addition, the first waiting time may be variously set by a user. For example, in a case of Japan, multiple first waiting times can be selectively set so as to correspond to the size of the object space 4 having, for example, 6 mats or 14 mats. In this case, the first waiting time may be set based on the maximum allowable value of the carbon dioxide concentration with respect to the living space or the carbon dioxide concentration at the time of starting the introduction of the outside air and based on the amount of ventilation air which is set in advance with respect to the living space.

In the embodiment, the second waiting time is set at a constant value. It is noted that, the second waiting time may be modified in response to the change rate and the change amount of $CO_2$ concentration. For example, in a case where the change rate is large, that is, in a case where the difference between the previous provisional reference value and the current provisional reference value is large, the $CO_2$ concentration is not completely decreased. In this case, the $CO_2$ concentration is expected to be further decreased after the second waiting time has elapsed again. For this reason, in this case, the subsequent second waiting time can be set at a longer period. In the present configuration, the power consumption can be reduced.

The time to calibrate the reference value may be set based on days and times as well. For example, it is considered that in a case of general homes or offices in a building, it is highly likely that a person is not present at midnight. In this case, it is considered that it is less likely that the reference value calibration process is interrupted, and thus there is no need to restart the reference value calibration process.

In the embodiment, in the case where a person is detected during the first waiting time (T1) or during the second waiting time (T2), the reference value calibration process is stopped. Herein, in the case where the reference value calibration process is stopped, the reference value calibration process may be performed again after a person is not detected any longer. Alternatively or in addition, the reference value calibration process may be performed again in the following day. Alternatively or in addition, the calibration of the reference value may be skipped once.

The object space 4 has a certain degree of size as a matter of course, and thus the air state may be different depending on the place. That is, it is likely that the distribution of the $CO_2$ concentration in the object space 4 is deviated. In addition to the above-described spatial factors, the acquired $CO_2$ concentration may be different due to an installation height of the controller 3 or the like. For this reason, the first waiting time may be set based on the calculated value as described above and based on the expected time required to make the air in the object space 4 uniform. In this case, the expected time can be acquired by, for example, a diffusion model of air.

The human sensor 12 and the $CO_2$ sensor 14 may be provided separately from the controller 3. The numerical values exemplified in the embodiment are merely one example, and the present disclosure is not limited thereto.

The present disclosure is not limited to the air conditioning system 1 exemplified in the embodiment. For example, various configurations may be employed in the present disclosure configured, which is to introduce the outside air into the object space 4, that is, configured to make the state in the object space 4 the same as the state of the outside air. For example, a discharge-side damper for discharging the air from the object space 4 may be provided. That is, the configuration described in FIG. 1 of the embodiment is merely one example, and the present disclosure is not limited thereto.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A $CO_2$ sensor reference value calibration apparatus comprising:
 a person detection unit configured to detect a person in an object space;
 a $CO_2$ sensor configured to acquire, as a relative value with respect to a preset reference value of the $CO_2$ sensor, a carbon dioxide concentration in the object space;
 a clock unit configured to measure a time; and
 a calibration unit configured to calibrate the reference value, wherein
 the calibration unit is configured to start introduction of outside air after a person is not detected in the object space,
 the calibration unit is configured to set, as a provisional reference value, a carbon dioxide concentration acquired when a preset first waiting time elapses after starting the introduction of the outside air,
 the calibration unit is configured to compare a carbon dioxide concentration, which is acquired when a preset second waiting time elapses after the setting of the provisional reference value, with the provisional reference value,
 the calibration unit is configured to repeatedly acquire the carbon dioxide concentration, when the second waiting time elapses after newly setting the acquired carbon dioxide concentration as the provisional reference value, in a case where a change rate of the carbon dioxide concentration is out of a preset allowable range, and
 the calibration unit is configured to set a currently set provisional reference value as the reference value in a case where the change rate of the carbon dioxide concentration is in the allowable range,
 the calibration unit is configured to compare the carbon dioxide concentration, which is acquired when the preset second waiting time elapses after the setting of the provisional reference value, with the provisional reference value,
 the calibration unit is configured to repeatedly acquire the carbon dioxide concentration, when the second waiting time elapses after the setting of the acquired carbon dioxide concentration as a new provisional reference value, in a case where the acquired carbon dioxide concentration is lower than the provisional reference value and where the change rate of the carbon dioxide concentration is negative, and
 the calibration unit is configured to set the currently set provisional reference value as the reference value in response to that the acquired carbon dioxide concentration is equal to or greater than the provisional reference value and that the change rate of the carbon dioxide concentration is positive.

2. The $CO_2$ sensor reference value calibration apparatus according to claim 1, wherein
 the calibration unit is configured to set, as the provisional reference value, a value acquired by correcting the acquired carbon dioxide concentration based on a preset error correction value.

3. The $CO_2$ sensor reference value calibration apparatus according to claim 1, wherein
 the first waiting time is set based on a maximum allowable value of the carbon dioxide concentration with respect to a living space and based on an amount of ventilation air defined in advance with respect to the living space.

4. The $CO_2$ sensor reference value calibration apparatus according to claim 1, wherein
 the first waiting time is set based on the carbon dioxide concentration when starting the introduction of the outside air and based on the preset amount of ventilation air with respect to the living space.

5. The CO2 sensor reference value calibration apparatus according to claim 1, wherein
 the calibration unit is configured to repeatedly acquire the carbon dioxide concentration, when the second waiting time elapses in a case where the acquired carbon dioxide concentration is equal to or greater than the provisional reference value, where the change rate of the carbon dioxide concentration is positive, and where the change rate of the carbon dioxide concentration is out of the preset allowable range.

6. The CO2 sensor reference value calibration apparatus according to claim 1, wherein
 the calibration unit is configured to repeatedly acquire the carbon dioxide concentration without setting the currently set provisional reference value as the reference value, when the second waiting time elapses after the setting of the acquired carbon dioxide concentration as a new provisional reference value, in a case response to that the acquired carbon dioxide concentration is lower than the provisional reference value and that the change rate of the carbon dioxide concentration is negative.

7. A $CO_2$ sensor reference value calibration apparatus comprising:
   a person detection unit configured to detect a person in an object space;
   a $CO_2$ sensor configured to acquire, as a relative value with respect to a preset reference value of the $CO_2$ sensor, a carbon dioxide concentration in the object space;
   a clock unit configured to measure a time; and
   a calibration unit configured to calibrate the reference value, wherein
   the calibration unit is configured to start introduction of outside air after a person is not detected in the object space,
   the calibration unit is configured to set, as a provisional reference value, a carbon dioxide concentration acquired when a preset first waiting time elapses after starting the introduction of the outside air,
   the calibration unit is configured to compare a carbon dioxide concentration, which is acquired when a preset second waiting time elapses after the setting of the provisional reference value, with the provisional reference value,
   the calibration unit is configured to repeatedly acquire the carbon dioxide concentration, when the second waiting time elapses after newly setting the acquired carbon dioxide concentration as the provisional reference value, in a case where a change rate of the carbon dioxide concentration is out of a preset allowable range,
   the calibration unit is configured to set a currently set provisional reference value as the reference value in a case where the change rate of the carbon dioxide concentration is in the allowable range,
   the calibration unit is configured to compare the carbon dioxide concentration, which is acquired when the preset second waiting time elapses after the setting of the provisional reference value, with the provisional reference value,
   the calibration unit is configured to repeatedly acquire the carbon dioxide concentration without setting the currently set provisional reference value as the reference value, when the second waiting time elapses after the setting of the acquired carbon dioxide concentration as a new provisional reference value, in a case where the acquired carbon dioxide concentration is lower than the provisional reference value and where the change rate of the carbon dioxide concentration is negative, and
   the calibration unit is configured to set the currently set provisional reference value as the reference value without elapse of the preset second waiting time in response to that the acquired carbon dioxide concentration is equal to or greater than the provisional reference value and that the change rate of the carbon dioxide concentration is positive.

8. A $CO_2$ sensor reference value calibration apparatus comprising:
   a person detection unit configured to detect a person in an object space;
   a $CO_2$ sensor configured to acquire, as a relative value with respect to a preset reference value of the $CO_2$ sensor, a carbon dioxide concentration in the object space;
   a clock unit configured to measure a time; and
   a calibration unit configured to calibrate the reference value, wherein
   the calibration unit is configured to start introduction of outside air after a person is not detected in the object space and on determination by the clock unit that it is a time for calibration of the reference value,
   the calibration unit is configured to set, as a provisional reference value, a carbon dioxide concentration acquired when a preset first waiting time elapses after starting the introduction of the outside air,
   the calibration unit is configured to compare a carbon dioxide concentration, which is acquired when a preset second waiting time elapses after the setting of the provisional reference value, with the provisional reference value,
   the calibration unit is configured to repeatedly acquire the carbon dioxide concentration, when the second waiting time elapses after newly setting the acquired carbon dioxide concentration as the provisional reference value, in a case where a change rate of the carbon dioxide concentration is out of a preset allowable range,
   the calibration unit is configured to set a currently set provisional reference value as the reference value in a case where the change rate of the carbon dioxide concentration is in the allowable range,
   the calibration unit is configured to compare the carbon dioxide concentration, which is acquired when the preset second waiting time elapses after the setting of the provisional reference value, with the provisional reference value,
   the calibration unit is configured to repeatedly acquire the carbon dioxide concentration without setting the currently set provisional reference value as the reference value, when the second waiting time elapses after the setting of the acquired carbon dioxide concentration as a new provisional reference value, in a case where the acquired carbon dioxide concentration is lower than the provisional reference value and where the change rate of the carbon dioxide concentration is negative, and
   the calibration unit is configured to set the currently set provisional reference value as the reference value without elapse of the preset second waiting time in response to that the acquired carbon dioxide concentration is equal to or greater than the provisional reference value and that the change rate of the carbon dioxide concentration is positive and suspends the calibration until the clock unit makes determination of the time for calibration next time.

* * * * *